United States Patent
Hong

(10) Patent No.: US 9,090,458 B2
(45) Date of Patent: Jul. 28, 2015

(54) ULTRASONIC TRANSDUCER AND METHOD OF MANUFACTURING THE SAME

(71) Applicant: Samsung Electronics Co., Ltd., Suwon-si (KR)

(72) Inventor: Seog-woo Hong, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 13/960,874

(22) Filed: Aug. 7, 2013

(65) Prior Publication Data

US 2014/0145275 A1    May 29, 2014

(30) Foreign Application Priority Data

Nov. 28, 2012  (KR) .................. 10-2012-0136553

(51) Int. Cl.
  B81B 3/00    (2006.01)
  B81C 1/00    (2006.01)
  B06B 1/02    (2006.01)
  G01N 29/24   (2006.01)

(52) U.S. Cl.
  CPC .......... B81C 1/00158 (2013.01); B06B 1/0292 (2013.01); B81C 1/00095 (2013.01); G01N 29/2406 (2013.01); B81B 2201/0271 (2013.01); B81B 2207/096 (2013.01)

(58) Field of Classification Search
  CPC ............... B81B 2201/0257; B81B 2203/04; B81B 3/0027; B81C 1/00158; B81C 1/00166; H04R 31/00; H04R 2201/003; H04R 2201/401; H04R 23/00
  USPC .............. 257/415, 416, 419, 254; 438/53; 381/150; 367/140–174
  See application file for complete search history.

(56) References Cited

U.S. PATENT DOCUMENTS

| | | |
|---|---|---|
| 2007/0180916 A1 | 8/2007 | Tian et al. |
| 2009/0122651 A1 | 5/2009 | Kupnik et al. |
| 2012/0074509 A1 | 3/2012 | Berg et al. |

FOREIGN PATENT DOCUMENTS

| | | |
|---|---|---|
| JP | 2006-295006 A | 10/2006 |
| JP | 2006-319712 A | 11/2006 |
| JP | 2007-198820 A | 8/2007 |
| JP | 2010-035134 A | 2/2010 |
| KR | 1020130076530 A | 7/2013 |

*Primary Examiner* — Whitney T Moore
(74) *Attorney, Agent, or Firm* — Sughrue Mion, PLLC

(57) ABSTRACT

An ultrasonic transducer and a method of manufacturing the same are disclosed. The ultrasonic transducer includes a conductive substrate, a projection which is disposed on the conductive substrate and which forms a cavity therein, a via hole which penetrates the projection and conductive substrate, a first electrode which includes a metal and which fills the via hole, a second electrode which is provided on a bottom of the conductive substrate, a membrane which is provided on the projection and which covers the cavity, and an upper electrode which is provided on the membrane and which contacts the first electrode.

27 Claims, 10 Drawing Sheets

ULTRASONIC TRANSDUCER AND METHOD OF MANUFACTURING THE SAME

CROSS-REFERENCE TO RELATED APPLICATIONS

This application claims priority from Korean Patent Application No. 10-2012-0136553, filed on Nov. 28, 2012, in the Korean Intellectual Property Office, the disclosure of which is incorporated herein by reference in its entirety.

BACKGROUND

1. Field

Exemplary embodiments relate to ultrasonic transducers and methods of manufacturing the same, and more particularly, to a capacitive micromachined ultrasonic transducer and a method of manufacturing the same.

2. Description of the Related Art

Micromachined ultrasonic transducers (MUTs) may convert electrical signals into ultrasonic signals, or may convert ultrasonic signals into electrical signals. Such MUTs are classified, depending on conversion methods which correspond thereto, into piezoelectric MUTs (PMUTs), capacitive MUTs (CMUTs), magnetic MUTs (MMUTs), etc. Among these, CMUTs have been drawing attention in the fields of medical image diagnostic apparatuses and sensors.

SUMMARY

Provided are methods and apparatuses which relate to a capacitive micromachined ultrasonic transducer and a method of manufacturing the same.

According to an aspect of one or more exemplary embodiments, an ultrasonic transducer includes a conductive substrate, a projection which is disposed on the conductive substrate and which forms a cavity inside of the conductive substrate, a via hole which penetrates the projection and conductive substrate, a first electrode which includes a metal, which first electrode fills the via hole, a second electrode which is provided on a bottom of the conductive substrate, a membrane which is provided on the projection and which covers the cavity, and an upper electrode which is provided on the membrane and which contacts the first electrode.

The projection may be formed integrally with the conductive substrate, for example, in a single body. Further, an oxide layer may be provided on a surface of the conductive substrate. In this case, the second electrode may contact a bottom portion of the conductive substrate which is exposed by the oxide layer.

The projection may include an oxide of the conductive substrate. In this case, an oxidation blocking layer may be provided on the conductive substrate inside the projection. Further, an oxide layer may be provided on a surface of the conductive substrate. In this case, the second electrode may contact a bottom portion of the conductive substrate which is exposed by the oxide layer.

The first electrode may extend toward the bottom of the conductive substrate.

The first electrode may fill the via hole by performing an electroplating method.

According to another aspect of one or more exemplary embodiments, a method for manufacturing an ultrasonic transducer includes forming a via hole in a conductive substrate such that the via hole penetrates the conductive substrate, bonding a wafer which includes a first substrate, an insulating layer, and a second substrate to a projection which is disposed on the conductive substrate, forming a first electrode layer on an inner wall of the via hole, forming a second electrode on a bottom of the conductive substrate, removing the insulating layer and the second substrate and forming a metal seed layer which connects to the first electrode layer on the first substrate, forming a first electrode by applying an electrical signal for electroplating to the metal seed layer and plating the inner wall of the via hole with metal, and forming an upper electrode on the first substrate such that the upper electrode contacts the first electrode.

The forming a via hole in a conductive substrate may include forming a first oxide layer by oxidizing the conductive substrate and patterning the first oxide layer, forming the projection by forming a second oxide layer by oxidizing the conductive substrate again, and removing the second oxide layer and then forming the via hole in a portion of the conductive substrate at which the projection is disposed. The method may further include, after the forming a via hole, forming a third oxide layer on a surface of the conductive substrate.

Further, the forming a via hole in a conductive substrate may include forming an oxidation blocking layer on the conductive substrate and patterning the oxidation blocking layer, forming the via hole in a portion of the conductive substrate which is exposed by the oxidation blocking layer such that the via hole penetrates the conductive substrate, and forming the projection by oxidizing the conductive substrate. In this case, the method may further include, before the forming an oxidation blocking layer, forming an oxide layer on the conductive substrate. The oxidation blocking layer may include a silicon nitride.

The wafer may include a silicon-on insulator (SOI) wafer.

The forming a metal seed layer may include forming a penetration hole which connects to the via hole in the first substrate, and depositing the metal seed layer on the first substrate such that the metal seed layer contacts a portion of the first electrode layer which is exposed by the penetration hole. The method may further include, after the forming a metal seed layer, forming a passivation layer on the metal seed layer.

The forming the upper electrode may include removing the passivation layer and then patterning the metal seed layer. Further, the upper electrode may be formed on the first substrate such that the upper electrode contacts the first electrode after the removing the passivation layer and the patterning the metal seed layer.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
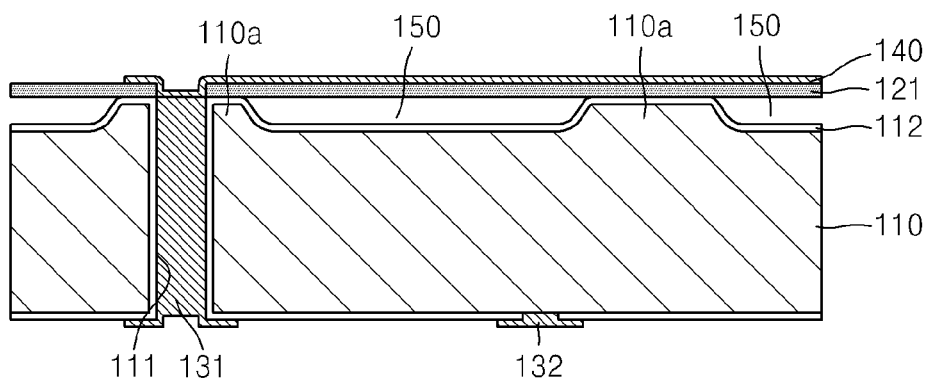
FIG. 1 is a view which illustrates an ultrasonic transducer, according to an exemplary embodiment.

Reference will now be made in detail to exemplary embodiments, examples of which are illustrated in the accompanying drawings. However, the present inventive concept is not limited to the exemplary embodiments illustrated hereinafter, and the exemplary embodiments herein are rather introduced to provide easy and complete understanding of the scope and spirit of example embodiments. In the drawings, like reference numerals denote like elements, and the thicknesses of layers and regions are exaggerated for clarity. Further, when it is described that a layer is present on a substrate or on another layer, the layer may be present being in direct contact with the substrate, or one or more other layers may be present therebetween. In addition, since because materials which form respective layers in the following exemplary embodiments are just exemplary, it is possible to use other materials in addition thereto.

FIG. 1 is a view which illustrates an ultrasonic transducer, according to an exemplary embodiment.

Referring to FIG. 1, the ultrasonic transducer includes a plurality of elements which are two-dimensionally arranged, each of the plurality of elements being capable of including at least one cavity 150. In FIG. 1, it is shown that one element includes a plurality of the cavities 150, but one element may include one cavity 150. The ultrasonic transducer includes a conductive substrate 110 and a membrane 121 which is provided on the conductive substrate 110.

On the conductive substrate 110, there are provided at least one projection 110a, and the cavities 150 are formed between and/or adjacent to the at least one projection 110a. The at least one projection 110a has the cavities 150 formed therein and simultaneously supports the membrane 121 which is disposed thereon. The at least one projection 110a may be formed integrally with the conductive substrate 110, for example, in a single body. The conductive substrate 110 functions as a lower electrode and, for example, may include a low-resistance silicon substrate, but the conductive substrate is not limited thereto. In a part of the conductive substrate 110, on which the at least one projection 110a is formed, there is formed a via hole 111. On a surface of the conductive substrate 110, there may be disposed an insulating layer 112. In particular, the insulating layer 112 may be formed on a top surface and a bottom surface of the conductive substrate 110 and on an inner wall of the via hole 111. The insulating layer may include, for example, a silicon oxide layer which may be formed by oxidizing the surface of the conductive substrate 110, but the insulating layer is not limited thereto.

The via hole 111 is filled with a first electrode 131 that is formed of at least one metal. The first electrode 131, as will be described later, may be formed by filling the inside of the via hole 111 with a metal by using an electroplating method. The first electrode 131 may extend toward a bottom of the conductive substrate 110. Further, a second electrode 132 is formed to be in contact with an exposed part of the bottom of the conductive substrate 110 via the insulating layer 112. The first and second electrodes 131 and 132, for example, may include one or both metals from among gold and copper, but the first and second electrodes 131 and 132 are not limited thereto, and may include various metallic materials in addition thereto.

On the at least one projection 110a of the conductive substrate 110, there is disposed the membrane 121. The membrane 121 is provided to cover the cavities 150 and may be supported by the at least one projection 110a. The membrane 121 may include, for example, silicon, but the membrane 121 is not limited thereto. In the membrane 121, a penetration hole which connects to the via hole 111 may be formed, through which a top surface of the first electrode 131 may be exposed. On the membrane 121, there is provided an upper electrode 140. The upper electrode 140 is provided to be in contact with a portion of the first electrode 131 which is exposed via the penetration hole. In the structure described above, a first predetermined voltage is applied to the upper electrode 140 via the first electrode 131 and a second predetermined voltage is applied to the conductive substrate 110 via the second electrode 132, thereby driving respective elements of the ultrasonic transducer.

In the present exemplary embodiment, because the via hole 111 which penetrates the conductive substrate 110 is filled with the first electrode 131 which includes at least one metal, it is not necessary to provide an electrode-penetrated substrate in order to transfer a driving signal to the conductive substrate 110. Further, when the inside of a via hole is vacant or an electrode-penetrated substrate is connected to a conductive substrate, unnecessary vacant spaces may exist, which may cause a distortion of an output signal in a high frequency area. However, in the present exemplary embodiment, because the inside of the via hole 111 which penetrates the conductive substrate 110 is filled with the first electrode 131 and there is no electrode-penetrated substrate which is connected to a conductive substrate, output characteristics in a high frequency area may be improved.

Figure 2:
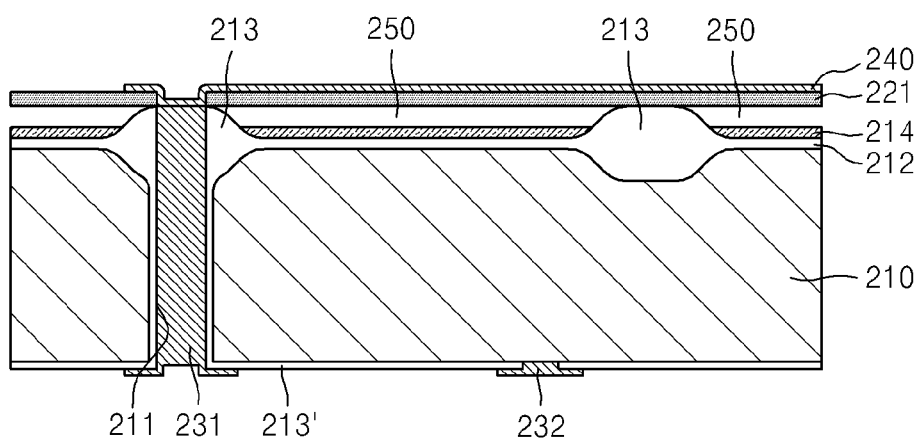
FIG. 2 is a view which illustrates an ultrasonic transducer, according to another exemplary embodiment.

FIG. 2 is a view which illustrates an ultrasonic transducer, according to another exemplary embodiment.

Referring to FIG. 2, the ultrasonic transducer includes a plurality of elements which are two-dimensionally arranged, each of the plurality of elements being capable of including at least one cavity 250. The ultrasonic transducer includes a conductive substrate 210 and a membrane 221 which is provided on the conductive substrate 210. At least one projection 213 is provided on the conductive substrate 210, and cavities 250 are provided between and/or adjacent to the at least one projection 213. The conductive substrate 210 may include, for example, a low-resistance silicon substrate, but the conductive substrate 210 is not limited thereto. The at least one projection 213 has the cavities 250 formed therein and simultaneously supports the membrane 221 provided thereon. The projection 213 may include an oxide of the conductive substrate 210. For example, the projection 213 may include a silicon oxide which is formed by oxidizing the low-resistance silicon substrate. On the conductive substrate 210 inside the at least one projection 213, there is provided an oxidation blocking layer 214. The oxidation blocking layer 214 may include, for example, a silicon nitride, but the oxidation blocking layer 214 is not limited thereto. Conversely, between the conductive substrate 210 and the oxidation blocking layer, there may be further provided a first oxide layer 212. The first oxide layer 212 may include, for example, a silicon oxide layer, but the first oxide layer 212 is not limited thereto.

A via hole 211 penetrates the projection 213 and the conductive substrate 210. Further, a second oxide layer 213', such as, for example, a silicon oxide layer, is formed on an inner wall of the via hole 211 and a bottom of the conductive substrate 210. A first electrode 231 which includes at least one metal is provided inside the via hole 211. The first electrode 231 may be formed by filling the inside of the via hole 211 with a metal by using an electroplating method. The first electrode 231 may extend toward the bottom of the conductive substrate 210. In addition, a second electrode 232 is formed to be in contact with an exposed part of the bottom of the conductive substrate 210 via the second oxide layer 213'. The first and second electrodes 231 and 232, for example, may include one or both metals from among gold and copper, but the first and second electrodes 231 and 232 are not limited thereto, and may include various metallic materials in addition thereto.

On the projection 213, there is disposed the membrane 221. The membrane 221 is provided to cover the cavities 250, and may be supported by the at least one projection 213. The membrane 221 may include, for example, silicon, but the membrane 221 is not limited thereto. In the membrane 221, a penetration hole which connects to the via hole 211 may be formed, through which a top surface of the first electrode 231 may be exposed. On the membrane 221, there is provided an upper electrode 240. The upper electrode 240 is provided to be in contact with a portion of the first electrode 231 which is exposed via the penetration hole. As described above, because the inside of the via hole 211 which penetrates the conductive substrate 210 is filled with the first electrode 231 and there is no electrode-penetrated substrate which connects to the conductive substrate 210, output characteristics in a high frequency area may be improved.

FIGS. 3, 4, 5, 6, 7, 8, 9, 10, 11, 12, 13, and 14 are views which illustrate a method for manufacturing the ultrasonic transducer of FIG. 1, according to an exemplary embodiment.

Figure 3:
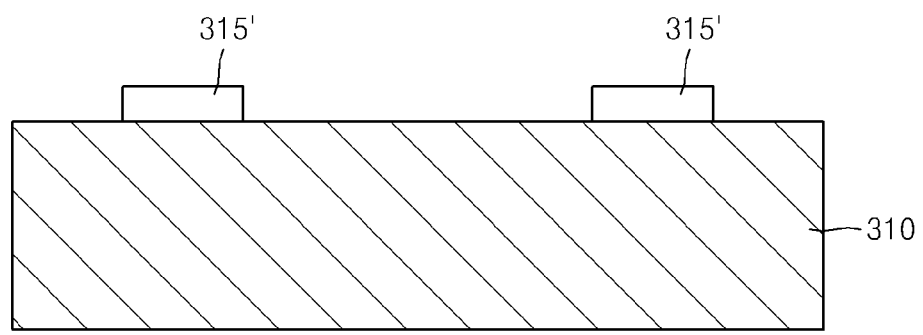
FIGS. 3, 4, 5, 6, 7, 8, 9, 10, 11, 12, 13, and 14 are views which illustrate a method for manufacturing an ultrasonic transducer, according to an exemplary embodiment.
Figure 4:
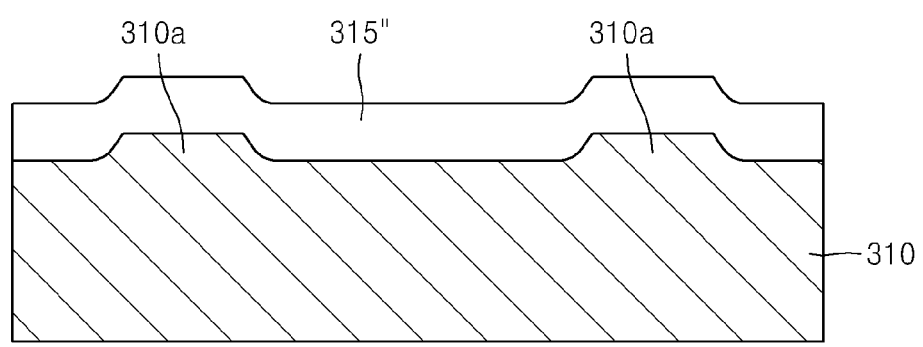
Figure 5:
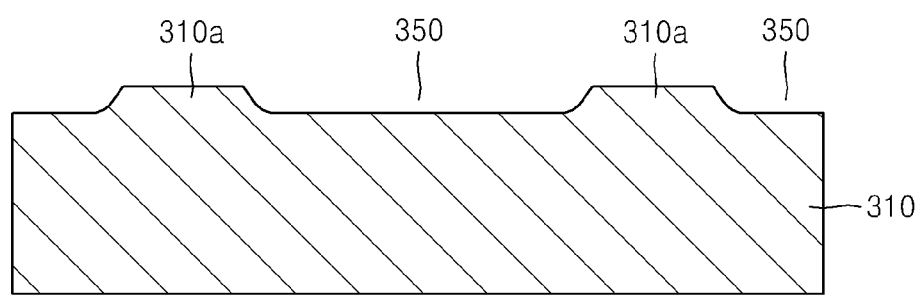

Referring to FIG. 3, a conductive substrate 310 is provided, and a first oxide layer 315' is formed on the conductive substrate 310. The conductive substrate 310 functions as a lower electrode and may include, for example, a low-resistance silicon substrate, but the conductive substrate is not limited thereto. The first oxide layer 315' may be formed by thermally oxidizing a top of the conductive substrate 310 in order to produce an oxide, and then patterning the oxide. Referring to FIG. 4, a second oxide layer 315" is formed by thermally oxidizing the top of the conductive substrate, on which the first oxide layer 315' is formed. As a result of or in conjunction with the formation of the second oxide layer 315", at least one projection 310a may be formed on the conductive substrate 310. Referring to FIG. 5, the second oxide layer 315", which had been formed on the top of the conductive substrate 310, is removed. Accordingly, cavities 350 may be formed between and/or adjacent to the at least one projection 310a of the conductive substrate 310.

Figure 6:
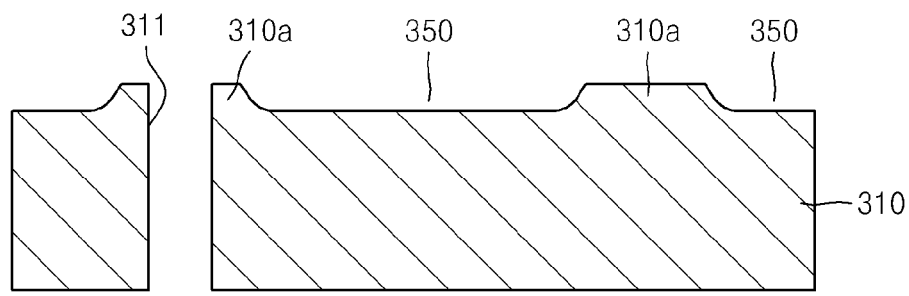
Figure 7:
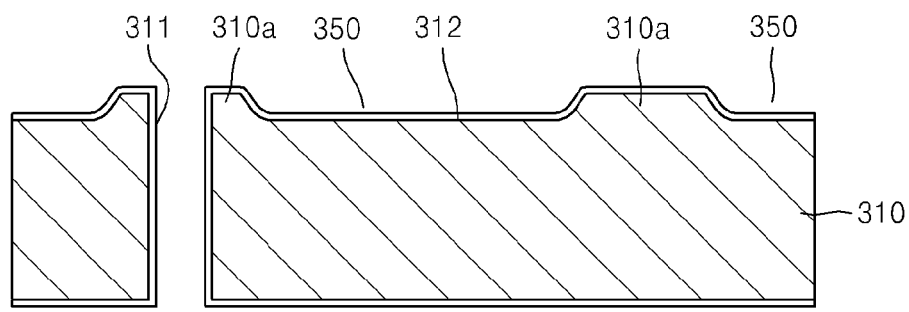

Referring to FIG. 6, a via hole 311 is formed such that the via hole 311 penetrates a part of the conductive substrate 310 on which one of the at least one projection 310a is formed. The via hole 311 may be formed by etching, such as, for example, inductively coupled plasma reactive ion etching (ICP_RIE), which etching is performed upon the conductive substrate 310. In this case, the via hole 311 may be formed with a diameter of about 40 μm, but this is just an example. Referring to FIG. 7, a third oxide layer 312 is formed by oxidizing a surface of the conductive substrate 310 which has been penetrated by the via hole 311. Accordingly, the third oxide layer 312 may be formed on the top and bottom of the conductive substrate 310 and an inner wall of the via hole 311.

Figure 8:
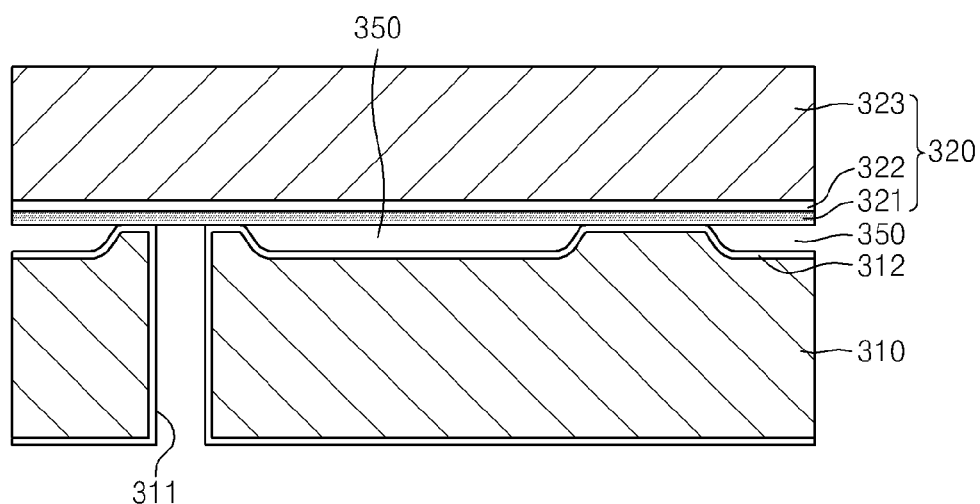

Referring to FIG. 8, a wafer 320 is bonded to the top of the conductive substrate 310, where the via hole 311 is formed, in particular, on the top of the at least one projection 310a. In this case, the wafer 320 may have a structure in which a first substrate 321, an insulating layer 322, and a second substrate 323 are sequentially stacked. For example, the wafer 320 may include a silicon-on insulator (SOI) wafer in which a first silicon substrate, an insulating layer, and a second silicon substrate are sequentially stacked. The bonding between the top of the projection 310a and the first substrate 321 of the wafer 320 may be performed by, for example, silicon direct bonding (SDB), but the bonding method is not limited thereto. Accordingly, the wafer 320 covers the cavities 350 which are formed on the conductive substrate 310, and the first substrate 321 forms a membrane of the ultrasonic transducer. The at least one projection 310a has the cavities 350 formed therein and simultaneously supports the first substrate 321.

Figure 9:
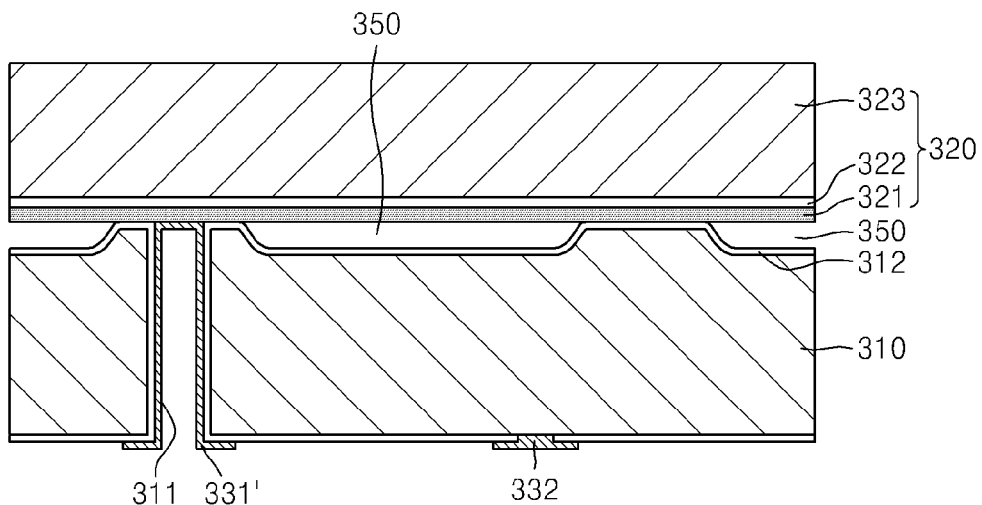
Figure 13:
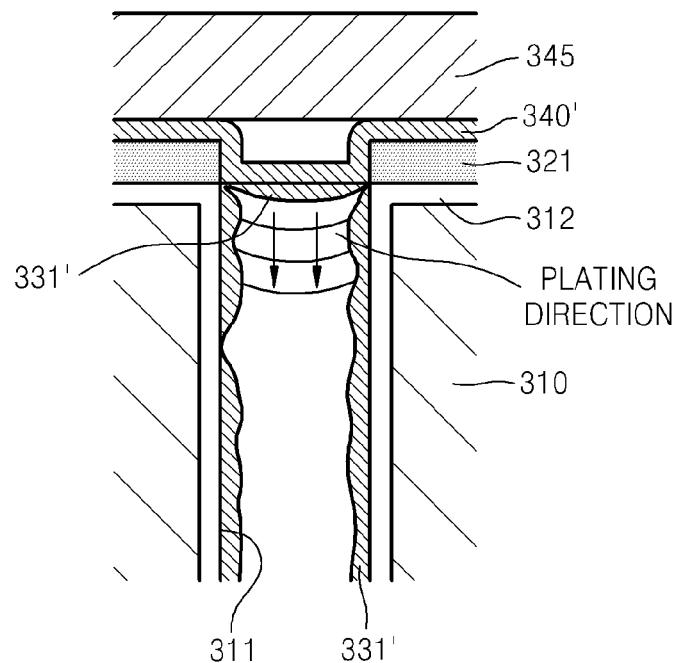

Referring to FIG. 9, a first electrode layer 331' is formed on the inner wall of the via hole 311, and a second electrode 332 is formed on the bottom of the conductive substrate 310. In particular, the third oxide layer 312 which has been formed on the bottom of the conductive substrate 310 is patterned, thereby exposing a part of the bottom of the conductive substrate 310. An electrode material layer (not shown) is deposited on the inner wall of the via hole 311 and the bottom of the conductive substrate 310 and patterned, thereby forming the first electrode layer 331' and the second electrode 332. Accordingly, the first electrode layer 331' is formed on a side wall and an upper wall of the via hole 311, and the second electrode 332 is formed on the third oxide layer 312 to be in contact with the bottom of the conductive substrate 310. The first electrode layer 331' may extend toward the bottom of the conductive substrate 310. Because the conductive substrate 310 generally has a very large thickness relative to a diameter of the via hole 311, for example, about 400 μm, the first electrode layer 331' may be unevenly deposited on the inner wall of the via hole 311, as shown in FIG. 13. The first electrode layer 331' and the second electrode 332 may include, for example, at least one metal from among gold and copper, but the first electrode layer 331' and the second electrode 332 are not limited thereto, and may include various metallic materials.

Figure 10:
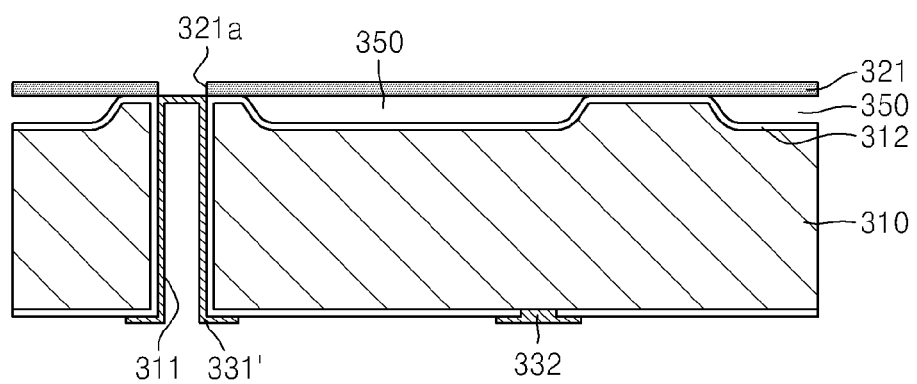
Figure 11:
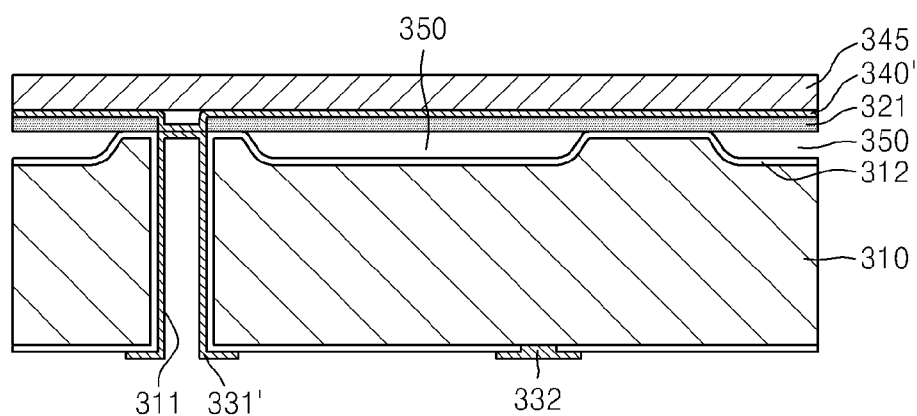

Referring to FIG. 10, the second substrate 323 and the insulating layer 322 have been removed and then the first substrate 321 is patterned, thereby forming a penetration hole 321a which connects to the via hole 311. Via the penetration hole 321a, the first electrode layer 331' which has been formed on an upper wall of the via hole 311 may be exposed. Referring to FIG. 11, a metal seed layer 340' is formed on the first substrate 321 to be in contact with the first electrode layer 331'. In this case, the metal seed layer 340' functions as an electrode to which an electric signal for electroplating is applied, as will be described further below. In addition, a passivation layer 345 is formed to cover the metal seed layer 340'. The passivation layer 345 functions to prevent a top of the metal seed layer 340' from being plated during an electroplating process. The passivation layer 345 may include, for example, an insulating material.

Figure 12:
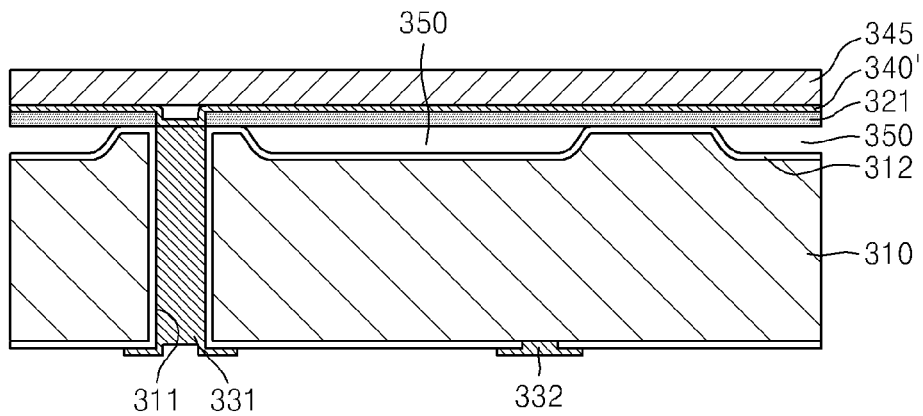

Referring to FIG. 12, the inside of the via hole 311 is plated with metal by using an electroplating process, thereby forming a first electrode 331. The first electrode 331 fills the inside of the via hole 311. FIG. 13 is a view which illustrates a process for forming the first electrode 331 inside the via hole 311 by using the electroplating process. Referring to FIG. 13, when an electric signal for electroplating is applied to the metal seed layer 340', plating starts from the portion of the first electrode layer 331' which is formed on the upper wall of the via hole 311, and the inside of the via hole 311 is gradually filled with metal. When the electroplating process is finished, the first electrode 331, which includes at least one metal, is formed inside the via hole 311. Similarly as with respect to the first electrode layer 331', the first electrode 331 may include at least one metal from among gold and copper, but the first electrode 331 is not limited thereto. The first electrode 331 may extend toward the bottom of the conductive substrate 310.

Figure 14:
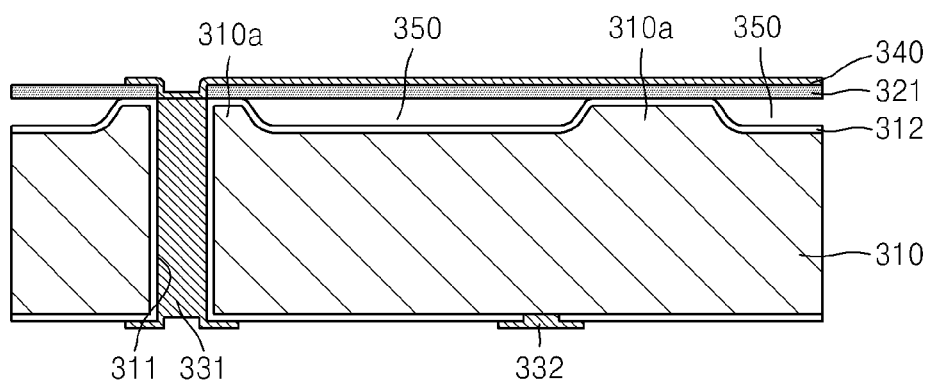

Referring to FIG. 14, the passivation layer 345 is removed from the metal seed layer 340' and then the metal seed layer 340' is patterned, thereby forming an upper electrode 340. In this case, the upper electrode 340 is formed on the first substrate 321 such that the upper electrode 340 connects to the first electrode 331. Conversely, the upper electrode 340 may be formed by removing the passivation layer 345 and the metal seed layer 340', thereby forming an electrode material layer (not shown) on the first substrate 321, and patterning the same.

As described above, by performing the method for manufacturing the ultrasonic transducer according to the present exemplary embodiment, before bonding the wafer 320 to the conductive substrate 310, the via hole 311 is previously formed in the conductive substrate 310. Accordingly, in forming the via hole 311 by etching the conductive substrate 310, a notch may be not formed, and it is possible to prevent an occurrence of an electrical disconnection between the upper electrode 340 and the first electrode 331. Further, the inside of the via hole 311 which is formed in the conductive substrate 310 is filled with the first electrode 331 by the electroplating process in such a way that it is unnecessary to provide an electrode-penetrated substrate for transferring a driving signal, thereby reducing manufacturing costs.

FIGS. 15, 16, 17, 18, 19, 20, 21, 22, 23, and 24 are views which illustrate a method for manufacturing the ultrasonic transducer, according to another exemplary embodiment. Hereinafter, only aspects that are different from the exemplary embodiment described above will be described.

Figure 15:
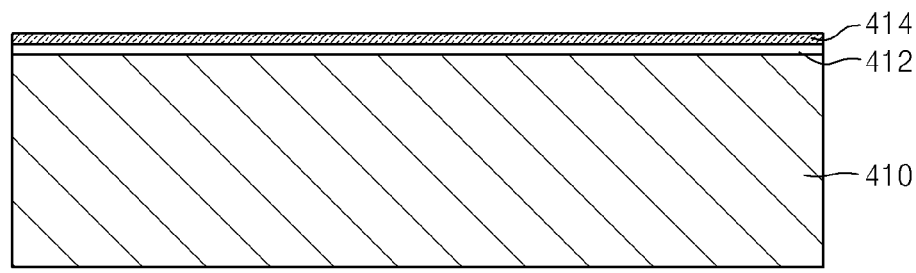
FIGS. 15, 16, 17, 18, 19, 20, 21, 22, 23, and 24 are views which illustrate a method for manufacturing an ultrasonic transducer, according to another exemplary embodiment.
Figure 16:
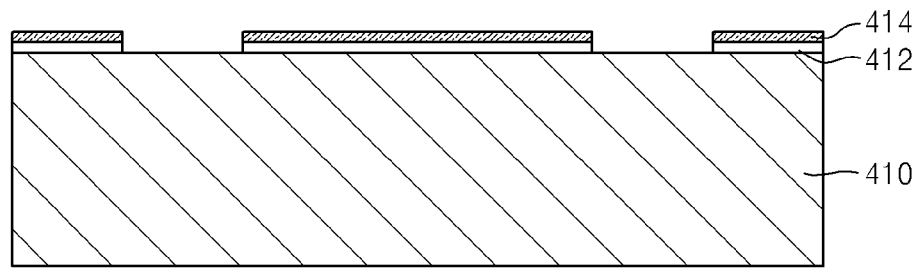

Referring to FIG. 15, a conductive substrate 410 is provided, and a first oxide layer 412 and an oxidation blocking layer 414 are sequentially formed on the conductive substrate 410. The conductive substrate 410 may include, for example, a low-resistance silicon substrate, but the conductive substrate 410 is not limited thereto. The first oxide layer 412 may include, for example, a silicon oxide, and the oxidation blocking layer 414 may include, for example, a silicon nitride, but the first oxide layer 412 and the oxidation blocking layer 414 are not limited thereto. Referring to FIG. 16, the oxidation blocking layer 414 and the first oxide layer 412 are patterned, thereby exposing parts of a top of the conductive substrate 410.

Figure 17:
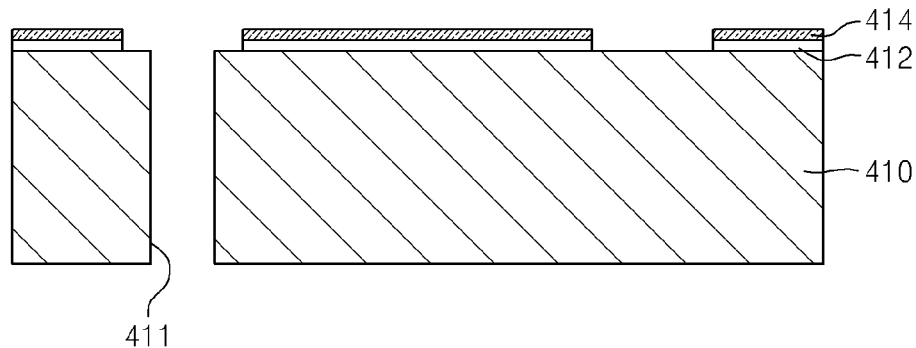
Figure 18:
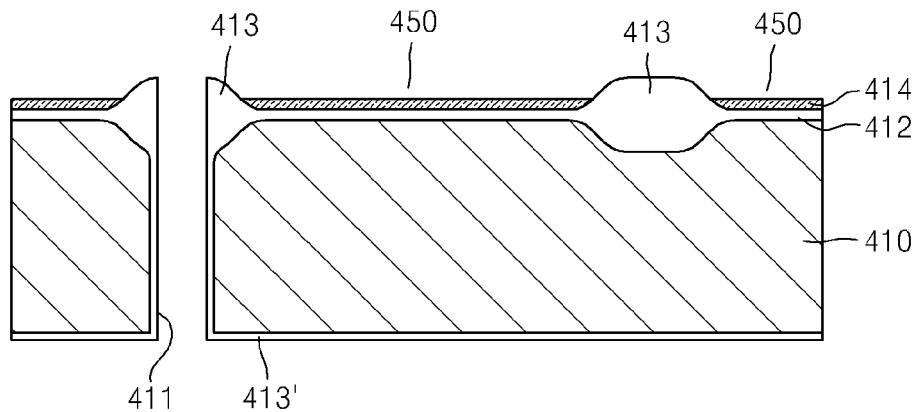

Referring to FIG. 17, a via hole 411 is formed such that the via hole 411 penetrates the exposed part of the top of the conductive substrate 410. Referring to FIG. 18, exposed parts of a surface of the conductive substrate 410 are thermally oxidized, thereby forming at least one projection 413. The at least one projection 413 may include an oxide of the conductive substrate 410, for example, a silicon oxide. Further, the via hole 411 penetrates the projection 413 and the conductive substrate 410, and a second oxide layer 413' is formed on an inner wall of the via hole 411 and a bottom of the conductive substrate 410. In this case, the at least one projection 413 and the second oxide layer 413' may include, for example, silicon oxides. It has been described above that the first oxide layer 412 and the oxidation blocking layer 414 are sequentially formed on the conductive substrate 410, the oxidation blocking layer 414 and the first oxide layer 412 are patterned, and the conductive substrate 410 is thermally oxidized. Conversely, although not shown in the drawings, the oxidation blocking layer 414 may be formed on the conductive substrate 410, the oxidation blocking layer 414 may be patterned, and the conductive substrate 410 may be thermally oxidized. In this case, on a part of the conductive substrate 410 which is positioned inside the projection 413, only the oxidation blocking layer 414 is formed.

Figure 19:
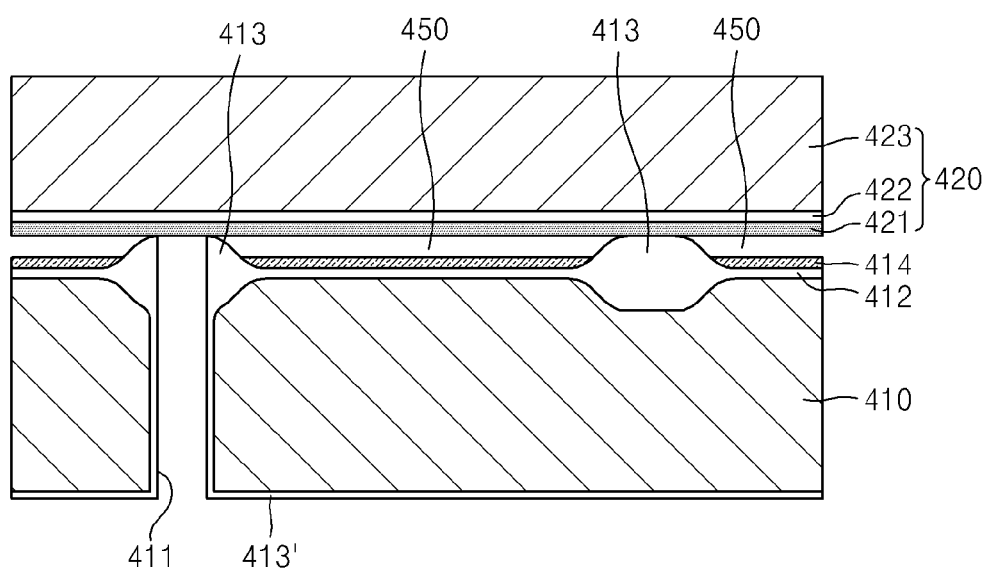

Referring to FIG. 19, a wafer 420 is bonded to a top of the at least one projection 413. In this case, the wafer 420 may have a structure in which a first substrate 421, an insulating layer 422, and a second substrate 423 are sequentially stacked. For example, the wafer 420 may include an SOI wafer in which a first silicon substrate, an insulating layer, and a second silicon substrate are sequentially stacked. In this case, the bonding between the top of the at least one projection 413 and the first substrate 421 of the wafer 420 may be performed by, for example, silicon direct bonding (SDB), but the bonding method is not limited thereto. Accordingly, the wafer 420 covers cavities 450 which are formed on the conductive substrate 410, and the first substrate 421 forms a membrane of the ultrasonic transducer. The at least one projection 413 has the cavities 450 formed therein and simultaneously supports the first substrate 421.

Figure 20:
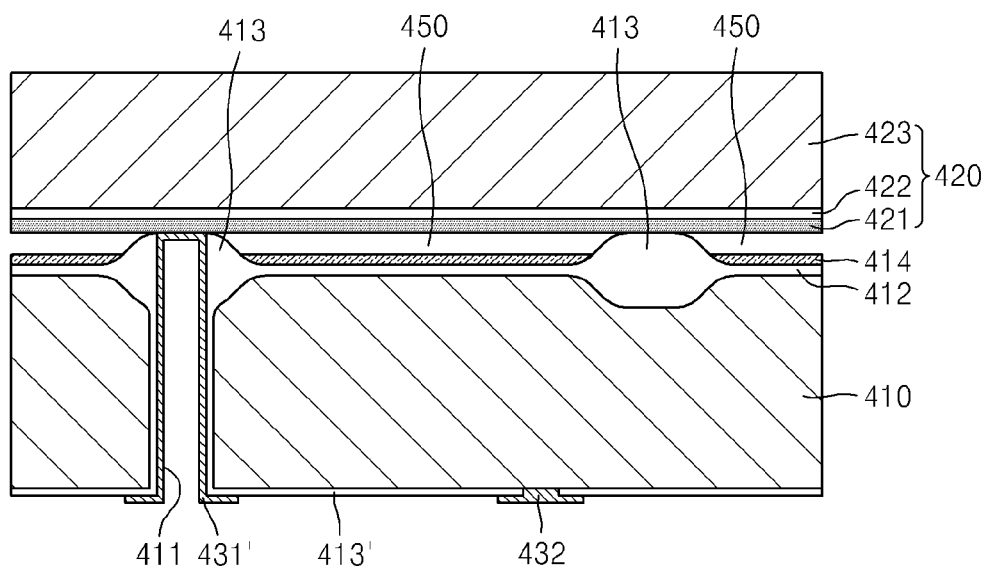

Referring to FIG. 20, a first electrode layer 431' is formed on the inner wall of the via hole 411, and a second electrode 432 is formed on the bottom of the conductive substrate 410. In particular, the second oxide layer 413' which is formed on the bottom of the conductive substrate 410 is patterned, thereby exposing a part of the bottom of the conductive substrate 410. An electrode material layer (not shown) is deposited on the inner wall of the via hole 411 and the bottom of the conductive substrate 410 and patterned, thereby forming the first electrode layer 431' and the second electrode 432. Accordingly, the first electrode layer 431' is formed on a side wall and an upper wall of the via hole 411, and the second electrode 432 is formed on the second oxide layer 413' to be in contact with the bottom of the conductive substrate 410. The first electrode layer 431' may extend toward the bottom of the conductive substrate 410. The first electrode layer 431' and the second electrode 432 may include, for example, at least one metal from among gold and copper, but the first electrode layer 431' and the second electrode 432 are not limited thereto, and may include various metallic materials.

Figure 21:
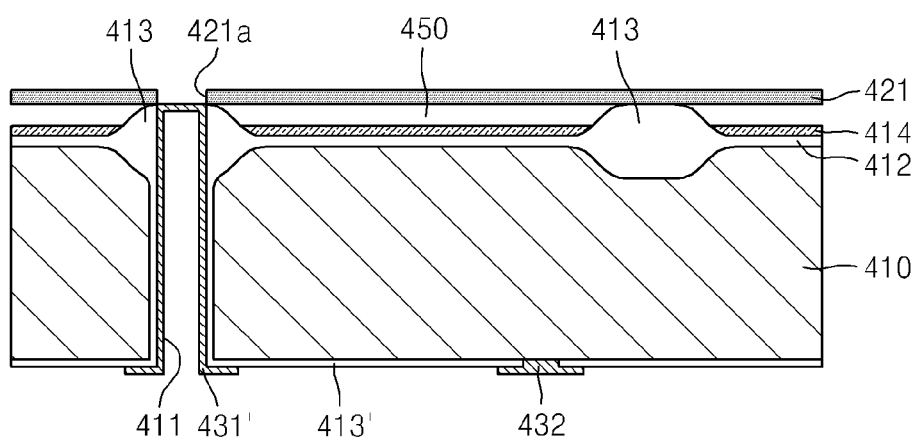
Figure 22:
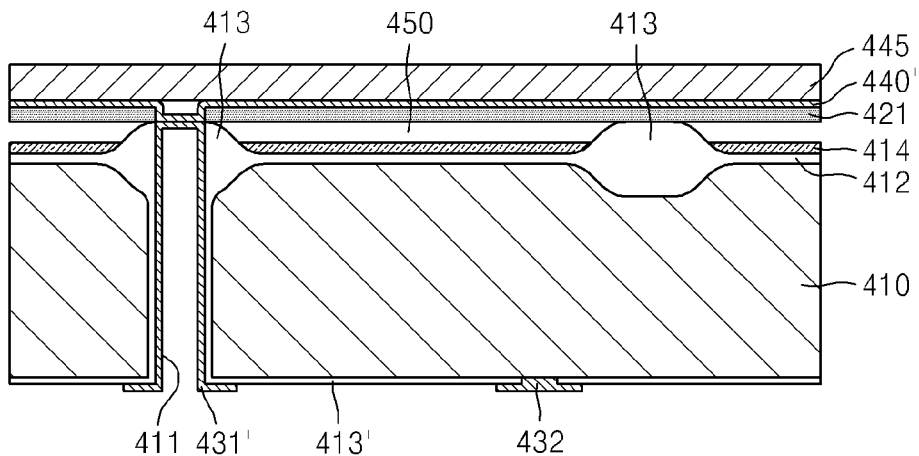

Referring to FIG. 21, the second substrate 423 and the insulating layer 422 are removed, and then the first substrate 421 is patterned, thereby forming a penetration hole 421a which connects to the via hole 411. Via the penetration hole 421a, the first electrode layer 431' which is formed on an upper wall of the via hole 411 may be exposed. Referring to FIG. 22, a metal seed layer 440' is formed on the first substrate 421 to be in contact with the first electrode layer 431', and then a passivation layer 445 is formed to cover the metal seed layer 440'. The passivation layer 445 functions to prevent a top of the metal seed layer 440' from being plated during an electroplating process, and may include, for example, an insulating material.

Figure 23:
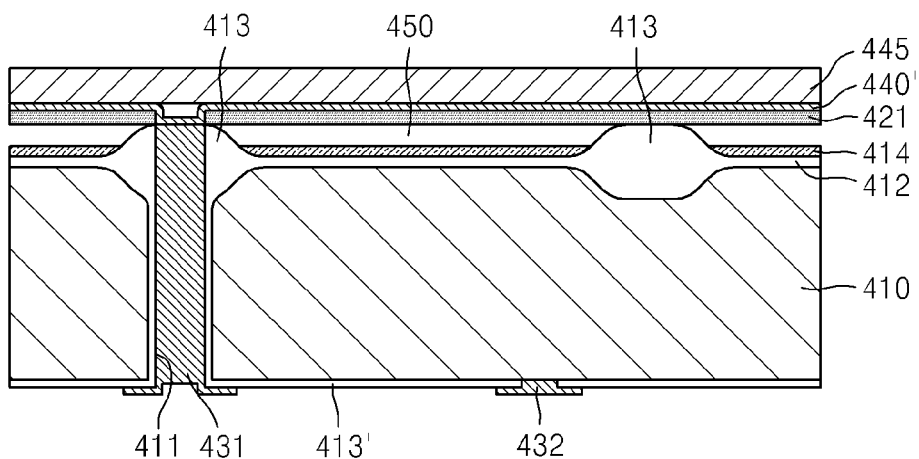

Referring to FIG. 23, the inside of the via hole 411 is plated with metal by using an electroplating process via the metal seed layer 440' and the first electrode layer 431', thereby forming a first electrode 431. In this case, the first electrode 431 fills the inside the via hole 411. In particular, when an electric signal for electroplating is applied to the metal seed layer 440', plating starts from a portion of the first electrode layer 431' which is formed on the upper wall of the via hole 411, and the inside of the via hole 411 is gradually filled with metal. When the electroplating process is finished, the first electrode 431, which includes at least one metal, is formed inside the via hole 411. Similarly as described above with respect to the first electrode layer 431', the first electrode 431 may include at least one metal from among gold and copper, but the first electrode 431 is not limited thereto. The first electrode 431 may extend toward the bottom of the conductive substrate 410.

Figure 24:
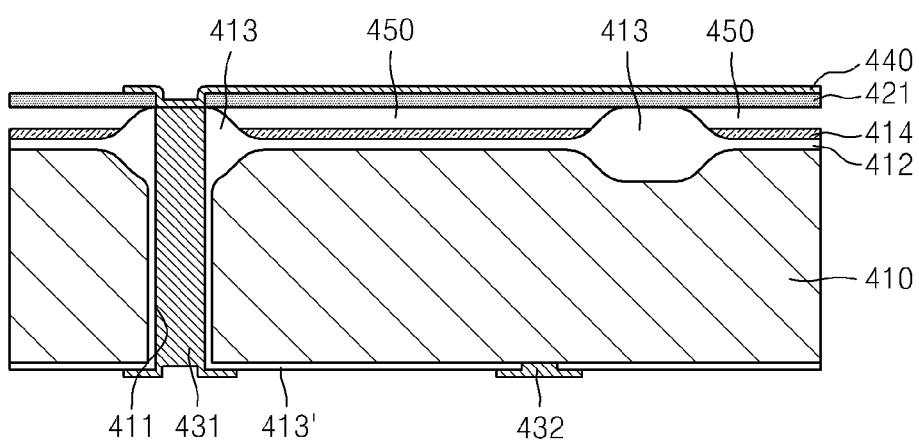

Referring to FIG. 24, the passivation layer 445 is removed from the metal seed layer 440' and then the metal seed layer 440' is patterned, thereby forming an upper electrode 440. The upper electrode 440 may be formed on the first substrate 421 such that the upper electrode 440 connects to the first electrode 431. Conversely, the upper electrode 440 may be formed by removing the passivation layer 445 and the metal seed layer 440', thereby forming an electrode material layer (not shown) on the first substrate 421, and patterning the same.

As a result of or in conjunction with performing the method for manufacturing the ultrasonic transducer according to the present exemplary embodiment, similarly as with respect to the exemplary embodiment described above, before bonding the wafer 420 to the conductive substrate 410, the via hole 411 is previously formed on the conductive substrate 410, thereby preventing an occurrence of an electrical disconnection between the upper electrode 440 and the first electrode 431. Further, the inside of the via hole 411 which is formed on the conductive substrate 410 is filled with the first electrode 431 by the electroplating process in such a way that it is unnecessary to provide an electrode-penetrated substrate for transferring a driving signal, thereby reducing manufacturing costs.

As described above, according to the one or more of the above exemplary embodiments, a first electrode which includes at least one metal is filled inside a via hole which penetrates a conductive substrate, thereby reducing manufacturing costs. Further, in cases in which the inside of a via hole is vacant or a conductive substrate is bonded to an electrode-penetrated substrate, unnecessary vacant spaces that may cause a distortion of an output signal in a high frequency area may exist. However, as described above with respect to the above exemplary embodiments, because the inside of the via hole which penetrates the conductive substrate is filled with the first electrode, and an electrode-penetrated substrate which is bonded to the conductive substrate is not needed, unnecessary spaces may be avoided. Accordingly, output characteristics in a high frequency area may be improved. In addition, in the method for manufacturing the ultrasonic transducer according to the above exemplary embodiments, before bonding a wafer to the conductive substrate, the via hole is previously formed on the conductive substrate, thereby preventing an occurrence of an electrical disconnection between an upper electrode and the first electrode.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. An ultrasonic transducer comprising:
    a conductive substrate;
    a projection which is disposed on the conductive substrate and which forms a cavity inside of the conductive substrate;
    a via hole which penetrates the projection and the conductive substrate;
    a first electrode which comprises a metal, which first electrode fills the via hole;
    a second electrode which is provided on a bottom of the conductive substrate;
    a membrane which is provided on the projection and which covers the cavity; and
    an upper electrode which is provided on the membrane and which contacts the first electrode.

2. The ultrasonic transducer of claim 1, wherein the projection is formed integrally with the conductive substrate.

3. The ultrasonic transducer of claim 2, wherein an oxide layer is provided on a surface of the conductive substrate.

4. The ultrasonic transducer of claim 3, wherein the second electrode contacts a bottom portion of the conductive substrate which is exposed by the oxide layer.

5. The ultrasonic transducer of claim 1, wherein the projection comprises an oxide of the conductive substrate.

6. The ultrasonic transducer of claim 5, wherein an oxidation blocking layer is provided on the conductive substrate inside the projection.

7. The ultrasonic transducer of claim 6, wherein an oxide layer is provided on a surface of the conductive substrate.

8. The ultrasonic transducer of claim 7, wherein the second electrode contacts a bottom portion of the conductive substrate which is exposed by the oxide layer.

9. The ultrasonic transducer of claim 1, wherein the first electrode extends toward the bottom of the conductive substrate.

10. The ultrasonic transducer of claim 1, wherein the first electrode fills the via hole by performing an electroplating method.

11. A method for manufacturing an ultrasonic transducer, the method comprising:
    forming a via hole in a conductive substrate such that the via hole penetrates the conductive substrate;
    bonding a wafer which comprises a first substrate, an insulating layer, and a second substrate to a projection which is disposed on the conductive substrate;
    forming a first electrode layer on an inner wall of the via hole;
    forming a second electrode on a bottom of the conductive substrate;
    removing the insulating layer and the second substrate and forming a metal seed layer which connects to the first electrode layer on the first substrate;
    forming a first electrode by applying an electrical signal for electroplating to the metal seed layer and plating the inner wall of the via hole with a metal; and
    forming an upper electrode on the first substrate such that the upper electrode contacts the first electrode.

12. The method of claim 11, wherein the forming the via hole in the conductive substrate comprises:
    forming a first oxide layer by oxidizing the conductive substrate and patterning the first oxide layer;
    forming the projection by forming a second oxide layer by oxidizing the conductive substrate again; and
    removing the second oxide layer and then forming the via hole in a portion of the conductive substrate at which the projection is disposed.

13. The method of claim 12, further comprising, after the forming the via hole, forming a third oxide layer on a surface of the conductive substrate.

14. The method of claim 11, wherein the forming the via hole in the conductive substrate comprises:
    forming an oxidation blocking layer on the conductive substrate and patterning the oxidation blocking layer;
    forming the via hole in a portion of the conductive substrate which is exposed by the oxidation blocking layer such that the via hole penetrates the conductive substrate; and
    forming the projection by oxidizing the conductive substrate.

15. The method of claim 14, further comprising, before the forming the oxidation blocking layer, forming an oxide layer on the conductive substrate.

16. The method of claim 14, wherein the oxidation blocking layer comprises a silicon nitride.

17. The method of claim 11, wherein the wafer comprises a silicon on insulator (SOI) wafer.

18. The method of claim 11, wherein the forming the metal seed layer comprises:
    forming a penetration hole which connects to the via hole in the first substrate; and depositing the metal seed layer on the first substrate such that the metal seed layer contacts a portion of the first electrode layer which is exposed by the penetration hole.

19. The method of claim 11, further comprising, after the forming the metal seed layer, forming a passivation layer on the metal seed layer.

20. The method of claim 19, wherein the forming the upper electrode comprises removing the passivation layer and then patterning the metal seed layer.

21. The method of claim 19, wherein the upper electrode is formed on the first substrate such that the upper electrode contacts the first electrode after the removing the passivation layer and the patterning the metal seed layer.

22. The method of claim 11, wherein the first electrode fills inside the via hole and extends toward the bottom of the conductive substrate.

23. An ultrasonic transducer, comprising:
   a conductive substrate which includes at least one projecting portion and at least one cavity portion which is adjacent to the at least one projecting portion;
   a first electrode which comprises at least one metal and which fills a via hole which penetrates the conductive substrate at one of the at least one projecting portion;
   a second electrode which is disposed on a bottom portion of the conductive substrate;
   a membrane which is disposed on the at least one projecting portion and which includes a penetration hole; and
   a third electrode which is disposed on the membrane and which contacts the first electrode via the penetration hole.

24. The ultrasonic transducer of claim 23, wherein the via hole is formed by performing an etching process upon the conductive substrate.

25. The ultrasonic transducer of claim 24, wherein the first electrode is formed by performing an electroplating process upon an inside of the via hole using at least one metal.

26. The ultrasonic transducer of claim 23, wherein the membrane is positioned between the third electrode and each of the at least one cavity portion of the conductive substrate.

27. The ultrasonic transducer of claim 23, wherein each of the first electrode, the second electrode, and the third electrode includes at least one metal from among gold and copper.

* * * * *